United States Patent
Larsen

(10) Patent No.: US 9,480,397 B2
(45) Date of Patent: Nov. 1, 2016

(54) GAZE TRACKING VARIATIONS USING VISIBLE LIGHTS OR DOTS

(71) Applicant: Sony Interactive Entertainment Inc., Tokyo (JP)

(72) Inventor: Eric J. Larsen, Pacifica, CA (US)

(73) Assignee: SONY INTERACTIVE ENTERTAINMENT INC., Tokyo (JP)

( * ) Notice: Subject to any disclaimer, the term of this patent is extended or adjusted under 35 U.S.C. 154(b) by 0 days.

(21) Appl. No.: 14/493,766

(22) Filed: Sep. 23, 2014

(65) Prior Publication Data

US 2015/0085251 A1    Mar. 26, 2015

Related U.S. Application Data

(60) Provisional application No. 61/881,662, filed on Sep. 24, 2013.

(51) Int. Cl.
| | | |
|---|---|---|
| A61B 3/14 | (2006.01) | |
| A61B 3/00 | (2006.01) | |
| A61B 3/113 | (2006.01) | |
| G06K 9/00 | (2006.01) | |

(52) U.S. Cl.
CPC ............. *A61B 3/113* (2013.01); *A61B 3/0008* (2013.01); *A61B 3/14* (2013.01); *G06K 9/00604* (2013.01)

(58) Field of Classification Search
USPC .................................................. 351/200–246
See application file for complete search history.

(56) References Cited

U.S. PATENT DOCUMENTS

| | | | |
|---|---|---|---|
| 5,016,282 A | 5/1991 | Tomono et al. | |
| 7,922,330 B2 | 4/2011 | Saarloos | |
| 2002/0051116 A1 | 5/2002 | Saarloos et al. | |
| 2005/0100191 A1 | 5/2005 | Harbach et al. | |
| 2008/0186449 A1 | 8/2008 | Sur et al. | |
| 2009/0196460 A1 | 8/2009 | Jakobs et al. | |
| 2010/0039618 A1* | 2/2010 | De Lemos | A61B 3/113 351/209 |
| 2010/0292676 A1 | 11/2010 | Larsen | |
| 2011/0006978 A1* | 1/2011 | Yuan | G06F 3/013 345/156 |
| 2011/0069277 A1 | 3/2011 | Blixt et al. | |
| 2011/0109880 A1 | 5/2011 | Nummela | |
| 2012/0086801 A1 | 4/2012 | Larsen | |
| 2012/0105486 A1 | 5/2012 | Lankford et al. | |

(Continued)

OTHER PUBLICATIONS

U.S. Appl. No. 14/493,723, to Eric J. Larsen, filed Sep. 23, 2014.

(Continued)

*Primary Examiner* — Mohammed Hasan
(74) *Attorney, Agent, or Firm* — Joshua D. Isenberg; JDI Patent

(57) ABSTRACT

Implementations of the present disclosure may include calibration techniques for systems which include eye tracking devices and display devices. The calibration techniques may involve a calibration process which utilizes a plurality of visible calibration targets that each defines a gaze point for a user. The calibration targets may include both targets output to the display device, as well as gaze points located on the eye tracking device itself. The calibration techniques may also include additional sensors on the eye tracking device to gather additional calibration information, such as a back-facing camera which captures images of the display device from the eye tracking device. Increased information regarding system setup that is useful in calibrating the eye tracking system may be obtained from the calibration process.

29 Claims, 9 Drawing Sheets

(56) References Cited

U.S. PATENT DOCUMENTS

| | | |
|---|---|---|
| 2012/0155703 A1 | 6/2012 | Hernandez-Abrego et al. |
| 2012/0257035 A1 | 10/2012 | Larsen |
| 2013/0096863 A1 | 4/2013 | Liu et al. |
| 2013/0321265 A1 | 12/2013 | Bychkov et al. |
| 2014/0055747 A1* | 2/2014 | Nistico .................. A61B 3/113 351/206 |
| 2014/0168401 A1 | 6/2014 | Bruijn et al. |
| 2014/0247232 A1* | 9/2014 | George-Svahn .......... G06F 3/02 345/173 |
| 2015/0208019 A1 | 7/2015 | Stewart et al. |

OTHER PUBLICATIONS

U.S. Appl. No. 14/493,738, to Eric J. Larsen, filed Sep. 23, 2014.
U.S. Appl. No. 61/881,656, to Eric J. Larsen, filed Sep. 24, 2013.
U.S. Appl. No. 61/881,660, to Eric J. Larsen, filed Sep. 24, 2013.
U.S. Appl. No. 61/881,662, to Eric J. Larsen, filed Sep. 24, 2013.
International Search Report and Written Opinion for International Application No. PCT/US2014/056998, dated Dec. 18, 2014.
International Search Report and Written Opinion for International Application No. PCT/US2014/057003, dated Dec. 4, 2014.
International Search Report and Written Opinion for International Application No. PCT/US2014/057006, dated Jan. 22, 2015.
Non-Final Office Action for U.S. Appl. No. 14/493,723, dated Sep. 15, 2015.
Non-Final Office Action for U.S. Appl. No. 14/493,723, dated Mar. 4, 2016.
Non-Final Office Action for U.S. Appl. No. 14/493,738, dated Jun. 6, 2016.
Notice of Allowance for U.S. Appl. No. 14/493,723, dated Jul. 14, 2016.

* cited by examiner

GAZE TRACKING VARIATIONS USING VISIBLE LIGHTS OR DOTS

CLAIM OF PRIORITY

This application claims the priority benefit of commonly-assigned U.S. provisional patent application No. 61/881,662 filed Sep. 24, 2013, the entire disclosures of which are incorporated herein by reference.

CROSS REFERENCE TO RELATED APPLICATIONS

This application is related to commonly-assigned, co-pending U.S. application Ser. No. 14/493,723, to Eric Larsen, entitled "GAZE TRACKING VARIATIONS USING DYNAMIC LIGHTING POSITION", filed the same day as the present application, the entire contents of which are incorporated herein by reference.

This application is related to commonly-assigned, co-pending U.S. application Ser. No. 14/493,738, to Eric Larsen, entitled "GAZE TRACKING VARIATIONS USING LEDs", filed the same day as the present application, the entire contents of which are incorporated herein by reference.

FIELD

The present disclosure relates to eye gaze tracking. In particular, aspects of the present disclosure relate to systems and methods for eye gaze tracking calibration using visible calibration targets.

BACKGROUND

Eye gaze tracking has use in a wide range of applications, including medical research, automobile technology, computer entertainment and video game programs, control input devices, augmented reality glasses, and more.

Some known eye gaze tracking techniques involve illuminating the eyes by emitting light from one or more light sources and detecting reflections of the emitted light off of the eyes with a sensor. Typically, this is accomplished using invisible light sources in the infrared range and capturing image data (e.g., images or video) of the illuminated eyes with an infrared sensitive camera. Image processing algorithms are then used to analyze the image data to determine eye gaze direction.

Generally, eye tracking image analysis takes advantage of characteristics distinctive to how light is reflected off of the eyes to determine eye gaze direction from the image. For example, the image may be analyzed to identify eye location based on corneal reflections in the image data, and the image may be further analyzed to determine gaze direction based on a relative location of the pupils in the image.

Two common gaze tracking techniques for determining eye gaze direction based on pupil location are known as Bright Pupil tracking and Dark Pupil tracking. Bright Pupil tracking involves illumination of the eyes with a light source that is substantially in line with the optical axis of the camera, causing the emitted light to be reflected off of the retina and back to the camera through the pupil. The pupil presents in the image as an identifiable bright spot at the location of the pupil, similar to the red eye effect which occurs in images during conventional flash photography. Dark Pupil tracking involves illumination with a light source that is substantially off line from the optical axis of the camera, causing light directed through the pupil to be reflected away from the optical axis of the camera, resulting in an identifiable dark spot in the image at the location of the pupil.

There are other known eye tracking techniques. For example, some eye tracking systems forgo the infrared light source and rely on environmental light to provide the reflections used to track the eye. Other more invasive techniques exist, such as techniques which rely on specialized contact lenses, which may also work in conjunction with a sensor such as an infrared camera.

With many of these eye tracking techniques, optimized performance of the tracking system is dependent upon accurate calibration of a variety of geometric parameters, particularly with reflection based techniques. Relevant calibration parameters may include both user eye parameters, such as iris size, eye curvature, pupil depth relative to the cornea, interpupillary distance (IPD), and iris texture, as well as geometric parameters of the system, such as relative light source location, sensor location, and a size and location of a display screen used in conjunction with the eye tracking system.

One way to calibrate eye tracking to a system's geometric parameters is to utilize a fixed geometric relationship between a display screen, a light source, and its sensor. For example, a display device may be provided with all of these components fixed in a common casing, in which case the relative locations of these components and the dimensions of the display screen would be known based on the specifications to which it is built. However, in many situations this is not an attractive solution because it restricts the ability of the eye tracking device (e.g., light source and/or sensor) to be provided independently from the display device, preventing such a tracking system from being used with preexisting displays and minimizing upgradability of the tracking device or the display independently from one another. Furthermore, it minimizes flexibility in how the system is set up and ties the tracking device to a particular display.

Another potential way to calibrate an eye tracking system is to have the user (i.e., end-user) manually input the calibration parameters after setting up the system's components. However, this would be a time consuming and unreliable process that would significantly detract from the user experience. Furthermore, the system would have to be recalibrated anytime the underlying calibration parameters were changed, e.g. if a component of the system were moved, further detracting from the user experience.

It is within this context that aspects of the present disclosure arise.

SUMMARY

An implementation of the present disclosure may include a method comprising: gathering eye tracking data during a calibration process with a sensor of an eye tracking device; and determining one or more calibration parameters from the eye tracking data, wherein the calibration process involves a plurality of visible calibration targets, wherein each said target defines a gaze point of the calibration process, wherein the plurality of targets includes one or more display targets and one or more sensor targets, wherein each of the one or more display targets defines a gaze point within an image output to a display device at a location known with respect to the image, wherein each of the one or more sensor targets defines a gaze point attached to the eye tracking device at a location known with respect to the eye tracking device, and wherein said determining the one or more calibration parameters includes determining one or more geometric parameters which fits the location of each of the gaze points defined by the one or more display targets, the location of each of the gaze points defined by the one or more sensor targets, and the eye tracking data gathered during the calibration process.

Another implementation of the present disclosure may include a system comprising: an eye tracking device having a sensor and one or more sensor targets; and a computing device coupled to the eye tracking device, wherein the system is configured to perform a method, the method comprising: gathering eye tracking data during a calibration process with the sensor of the eye tracking device; and determining, with the computing device, one or more calibration parameters from the eye tracking data, wherein the calibration process involves the one or more sensor targets and one or more display targets, wherein each said target defines a gaze point of the calibration process, wherein each of the one or more display targets defines a gaze point within an image output to a display device at a location known with respect to the image, wherein each of the one or more sensor targets defines a gaze point attached to the eye tracking device at a location known with respect to the eye tracking device, and wherein said determining the one or more calibration parameters includes determining one or more geometric parameters of the system which fits the location of each of the gaze points defined by the one or more display targets, the location of each of the gaze points defined by the one or more sensor targets, and the eye tracking data gathered during the calibration process.

Another implementation of the present disclosure may include a non-transitory computer readable medium having processor-executable instructions embodied therein, wherein execution of the instructions by a processor causes a processor to perform a method, the method comprising: gathering eye tracking data during a calibration process with a sensor of an eye tracking device; and determining one or more calibration parameters from the eye tracking data, wherein the calibration process involves a plurality of visible calibration targets, wherein each said target defines a gaze point of the calibration process, wherein the plurality of targets includes one or more display targets and one or more sensor targets, wherein each of the one or more display targets defines a gaze point within an image output to a display device at a location known with respect to the image, wherein each of the one or more sensor targets defines a gaze point attached to the eye tracking device at a location known with respect to the eye tracking device, and wherein said determining the one or more calibration parameters includes determining one or more geometric parameters which fits the location of each of the gaze points defined by the one or more display targets, the location of each of the gaze points defined by the one or more sensor targets, and the eye tracking data gathered during the calibration process.

Another implementation of the present disclosure may include a method comprising: gathering eye tracking data during a calibration process with a first sensor of an eye tracking device; gathering calibration data with a second sensor of an eye tracking device; and determining one or more calibration parameters from the eye tracking data and the calibration data, wherein the calibration process involves a plurality of visible calibration targets, wherein each said target defines a gaze point of the calibration process, wherein the plurality of targets includes one or more display targets, wherein each of the one or more display targets defines a gaze point within an image output to a display device at a location known with respect to the image, and wherein said determining the one or more calibration parameters includes determining one or more geometric parameters which fits the location of each of the gaze points defined by the one or more display targets, the calibration data gathered with the second sensor, and the eye tracking data gathered during the calibration process.

Another implementation of the present disclosure may include a system comprising: an eye tracking device, the eye tracking device having one or more light sources, a front-facing camera that is sensitive to light emitted from the one or more light sources, and a back-facing camera.

Another implementation of the present disclosure may include a non-transitory computer readable medium having processor-executable instructions embodied therein, wherein execution of the instructions by a processor causes a processor to perform a method, the method comprising: gathering eye tracking data during a calibration process with a first sensor of an eye tracking device; gathering calibration data with a second sensor of an eye tracking device; and determining one or more calibration parameters from the eye tracking data and the calibration data, wherein the calibration process involves a plurality of visible calibration targets, wherein each said target defines a gaze point of the calibration process, wherein the plurality of targets includes one or more display targets, wherein each of the one or more display targets defines a gaze point within an image output to a display device at a location known with respect to the image, and wherein said determining the one or more calibration parameters includes determining one or more geometric parameters which fits the location of each of the gaze points defined by the one or more display targets, the calibration data gathered with the second sensor, and the eye tracking data gathered during the calibration process.

BRIEF DESCRIPTION OF THE DRAWINGS

The teachings of the present disclosure can be readily understood by considering the following detailed description in conjunction with the accompanying drawings, in which.

DETAILED DESCRIPTION

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

Introduction

Aspects of the present disclosure related to calibration of an eye tracking device that involves a plurality of visual calibration targets. Each calibration target may define a gaze point for a user of the eye tracking device, and a sensor of the eye tracking device may gather eye tracking data of the user during the calibration process in order to determine calibration parameters which may be variable among different system setups.

In implementations of aspects of the present disclosure, the calibration targets may include display targets which are output to a display device, each display target defining a gaze point in a location of display screen, as well as a sensor target attached to the eye tracking device, which defines a gaze point in a known location relative to the eye tracking device. A calibration process that involves a user gazing at each of the different calibration targets may provide additional information useful to the calibration process than would be provided with only display of visual targets on the display device alone.

Further implementations of aspects of the present disclosure may include eye tracking devices which utilize a plurality of sensors on the eye tracking device. By way of example, an eye tracking device may include a front-facing infrared camera to capture images of eye reflections which may be analyzed to determine eye gaze parameters, as well as a back-facing camera to capture images of a display device, in order to obtained additional calibration information relevant to the set-up of the system.

Implementation Details

Figure 1A:
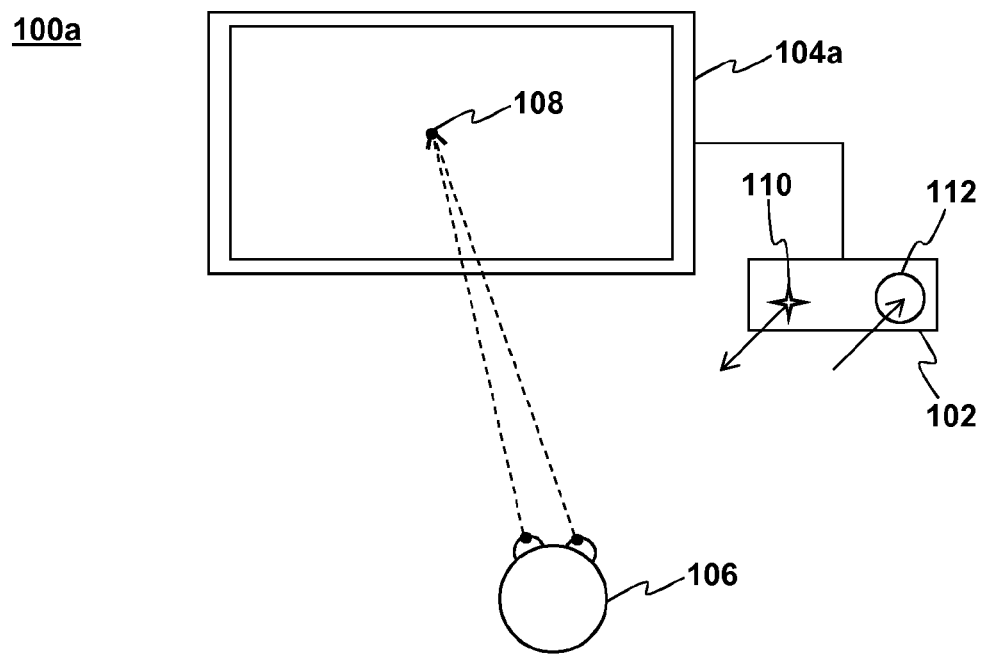
FIG. 1A is a schematic diagram depicting a system having an eye tracking device and a display device to illustrate various aspects of the present disclosure.

A schematic diagram of system for eye tracking is depicted in FIG. 1A to illustrate various aspects of the present disclosure. The example system 100a of FIG. 1A includes an eye tracking device 102 and a display device 104a, the two of which may be set up to operate in coordination with each other to track the eyes of a user 106 and correlate the eye tracking to images output to the display 104a. By way of example, and not by way of limitation, the eye tracking device 102 may be used to determine a gaze point 108 of the user 106, and correlate the user's gaze point 108 to images output to the display device 104a, e.g., to determine which objects in the images the user may be gazing at and/or to control aspects of the images based on the user's gaze.

The eye tracking device 102 may include a light source 110 and a sensor 112 which is sensitive to light emitted from the light source. By way of example, the light source 110 may be an invisible light source, such as one or more infrared light-emitting diodes (LEDs), and the sensor 112 may be an image capture device sensitive to the invisible light emitted from the invisible light source, such as an infrared camera. The illustrated eye tracking device 102 may gather eye tracking data by emitting light from the light source 110 and detecting an area illuminated by the emitted light with the sensor 112, e.g., by capturing images of the area illuminated by the emitted light. The eye tracking data gathered by the sensor 112 may then be analyzed to determine various characteristics of the user's eye or eyes, such as eye position, eye movements, gaze direction, gaze point 108, or some combination thereof.

These characteristics of the user's eyes may be determined by analysis of the of the eye tracking data with a computing device (not separately pictured) coupled to the sensor 112 of eye tracking device, in order to process the eye tracking data gathered by the sensor 112 and determine one or more characteristics of the user's eyes. By way of example, the processing device may be a separate unit or embedded in the eye tracking device itself.

Figure 1B:
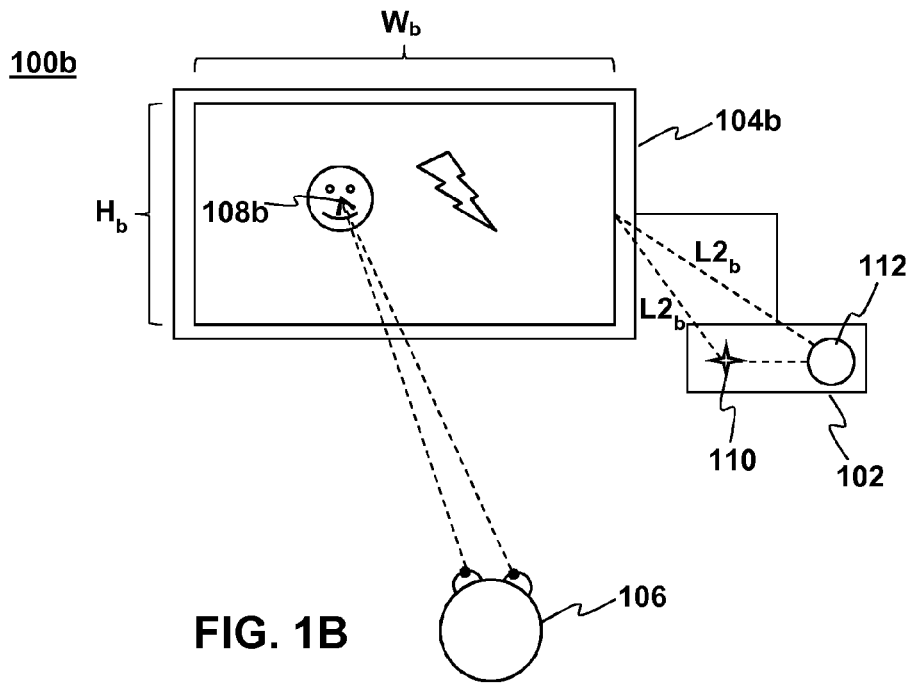
FIGS. 1B-1C are schematic diagrams depicting systems which have eye tracking devices and display devices set up in different geometric configurations to illustrate various aspects of the present disclosure.
Figure 1C:
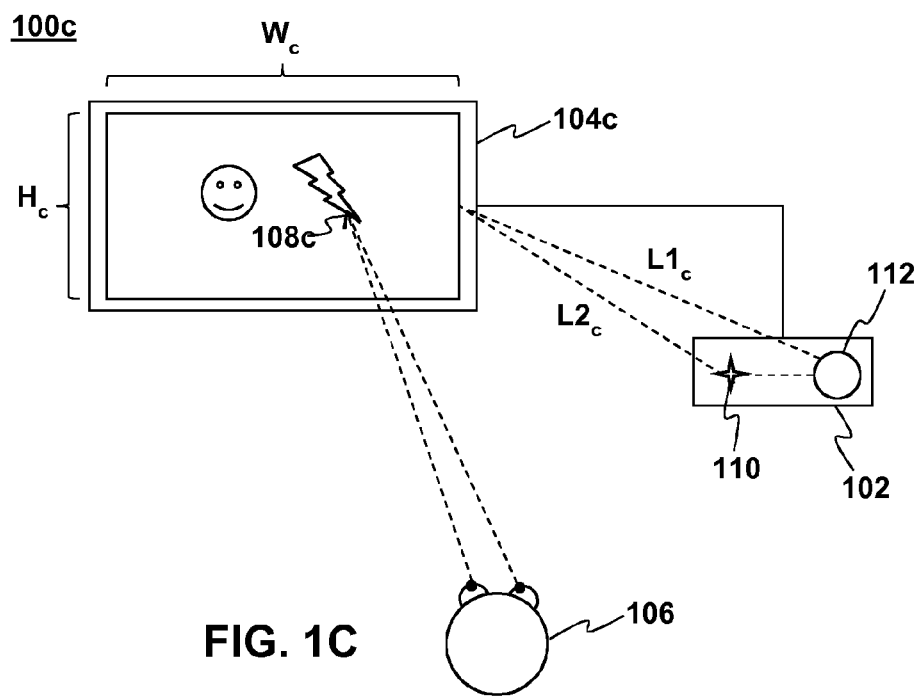

Additional schematic diagrams of systems for eye tracking that are illustrative of further aspects of the present disclosure are depicted in FIGS. 1B-1C. The example systems 100b and 100c of FIGS. 1B and 1C, respectively, illustrate similar eye tracking systems that are set up with different geometric parameters.

In the examples depicted in FIGS. 1B-1C, each of the eye tracking devices 102 is provided as a separate unit from its corresponding display device 104a,b, and each eye tracking device 102 does not form an integral unit with its corresponding display device 104b,c (e.g., sensors and light sources of the eye tracking devices are not built into the display devices). As a result, various geometric parameters of the systems 100b,c are not known prior to setup but rather may be variable between different setups, as shown in the different configurations 100a and 100b depicted in FIGS. 1B-1C. For example, the illustrated systems 100b,c have different display devices 104b,c having different screen dimensions $W_b$, $H_b$ and $W_c$, $H_c$, respectively, which results in different display screen sizes and different output image sizes relative to the user's eyes. Likewise, in the illustrated example, the relative locations $L1_b$, $L2_b$ and $L1_c$, $L2_c$ (e.g., relative distances and/or three-dimensional orientations) of eye tracking device components relative to the display devices 104b,c are different. As a result, these different geometric parameters may affect the accuracy of the eye tracking and how eye tracking data gathered with the eye tracking device is analyzed to determine characteristics of the eyes of the user 106.

By way of example, and not by way of limitation, in the example configurations 100b and 100c of FIGS. 1B and 1C, the user's eye gaze direction relative to the eye tracking device 102 is depicted as being the same in the different configurations. In particular, the location of the light source 110, the location of the sensor 112, the location of the user 106, and the gaze direction of the user 106 are all the same relative to one another in the two configurations 100b and 100c. As a result, eye tracking data gathered with the sensor 112, such infrared images containing reflections of emitted infrared light off of the user's eyes, will appear the same. However, in the configuration 100b depicted in FIG. 1B, the user's gaze point 108b on the image output to the display device 104b is different from the gaze point 108c of the user in the setup 100c depicted in FIG. 1C. As a result, analysis of the eye tracking data received from the sensor 112 of the eye tracking device 102 to determine eye characteristics, such as a display screen gaze point, is dependent upon the geometric parameters of the system. It would be desirable to calibrate the systems to account for these differences and other differences in calibration parameters so that eye tracking data gathered with the eye tracking device may be accurately processed.

A schematic diagram of a calibration process for a system for eye tracking 200 is depicted in FIGS. 2A-2D to illustrate various aspects of the present disclosure. The example calibration process of FIGS. 2A-2D involves a plurality of visual calibration targets in different locations, wherein each of the calibration targets defines a gaze point for a user during the calibration process. In the illustrative calibration process of FIGS. 2A-2D, the calibration targets include both visible targets 220a,b,d that are contained within images output to the display device, referred to herein as "display targets," and a visible target 222 that is attached to the eye tracking device, referred to herein as "sensor targets."

Turning to FIGS. 2A-2D in more detail, the calibration process may begin by outputting an image to the display device 204 which contains an initial visual calibration target 220a. It is noted that any arbitrary image may be used as the display target 220a in order to define a gaze point for a user's vision. In the implementation depicted in FIG. 2A, the visual calibration target 220a is depicted as a dot contained within a calibration image that is output to the display device 204, and the location of this dot relative to the display screen may be known. In one example, its location may be known because it is pre-defined in a calibration program that outputs calibration targets to the display device as images. In another example, its location may be known because its location is defined by user input, and the location within the image is known from the user input.

During the calibration process, a user 206 may look at this visual target 220a, and the eye tracking device 202 may gather eye tracking data while the user is looking at the gaze point defined by the calibration target 220a. The eye tracking device 202 may gather the data, for example, by emitting light from the light sources 210 and detecting an area illuminated by the light sources with the sensor 212, e.g., to obtain images of reflections of the emitted light off of the user's eyes. This portion of the eye tracking data may be correlated with the initial calibration target 220a (e.g. based on correspondence between the time at which this portion of eye tracking data was gathered and the time at which the calibration target 220a was visible on the display device 204).

Figure 2A:
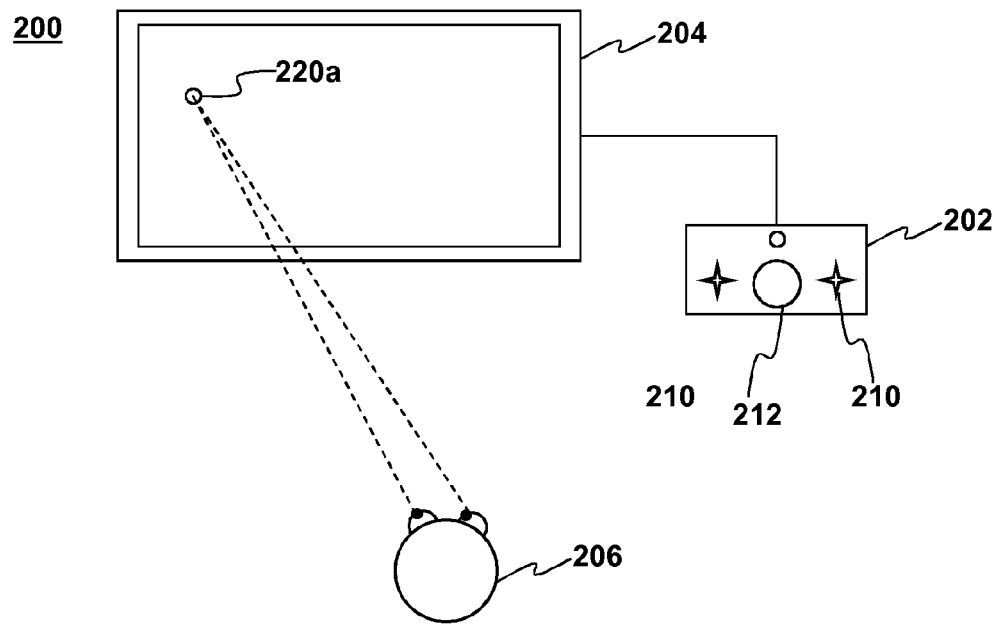
FIGS. 2A-2D are schematic diagrams depicting an example calibration process for a system similar to the systems depicted in FIGS. 1A-1C to illustrate various aspects of the present disclosure.
Figure 2B:
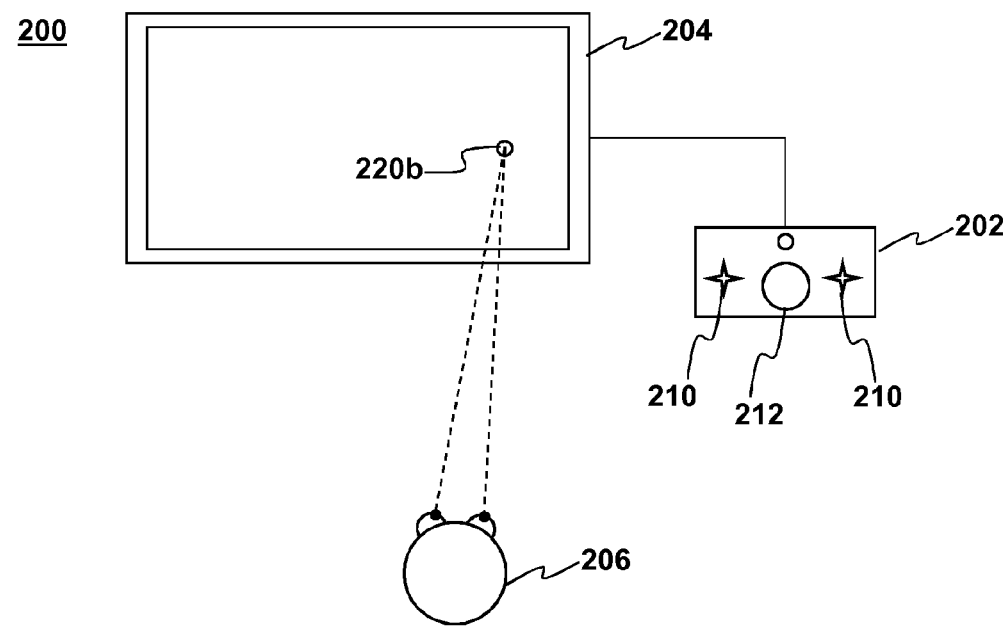

As depicted in FIG. 2B, the calibration process may involve another display target 220b defining an additional gaze point on the display screen of the display device 204, at a different location from the initial calibration target 220a. The user 206 may then look at this additional visual target 220b, and additional eye tracking data may be gathered with the eye tracking device 202 and correlated with this additional target 220b, e.g., as described above with reference to FIG. 2A.

Figure 2C:
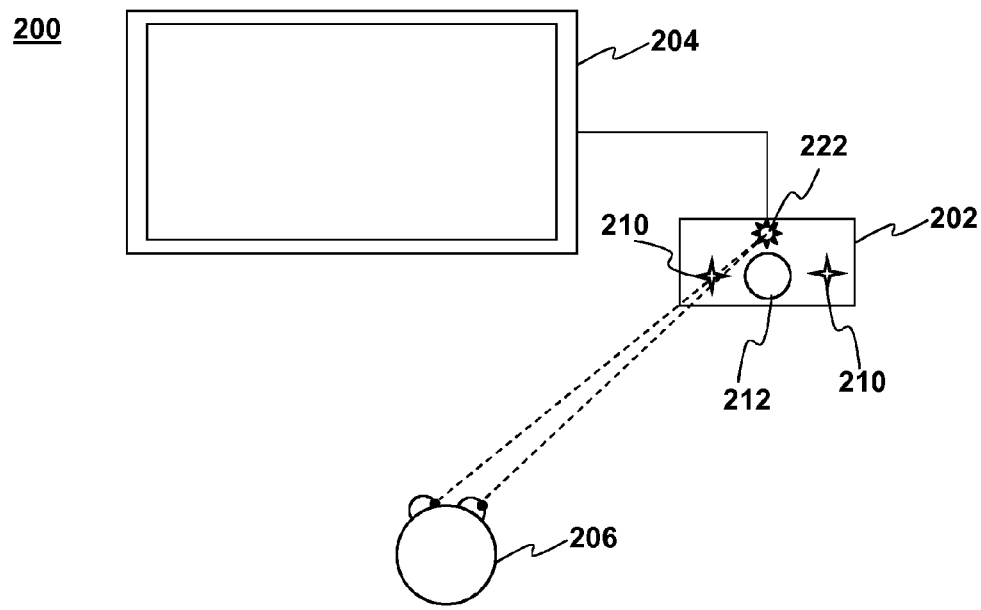

As depicted in FIG. 2C, the calibration process may involve yet another visual calibration target 222; however, in contrast to the display targets 220a and 220b, which have gaze points that are defined relative to an output image, the illustrated visual calibration target 222 is a sensor target that is attached to the eye tracking device 202 in a known location, and the gaze point of the sensor target is defined relative to the eye tracking device 202, e.g., relative to the sensor 212 that gathers the eye tracking data. During the calibration process of FIGS. 2A-2D, eye tracking data of the user 206 gazing at this sensor target 222 may be gathered and correlated to the sensor target, e.g., in a similar manner as described above.

This sensor target 222 may take a variety of forms, any of which may define a gaze point in a known location relative to the eye tracking device 202. In one example, this sensor target 222 is in the form of a visible light source, such as an LED in the visible spectrum. This LED may be attached to the sensor 212, such as by being fixed to casing of the eye tracking device 202 in a known location, and this LED may be illuminated at a corresponding time during the calibration process so that the user 206 may affix a gaze upon the visible illuminated LED. In another example, the sensor target 222 is in the form of a physical marking made onto the eye tracking device, such as a sticker, printing, etching, etc., that is prominent enough to be visible to a user. In yet another example, the sensor target 222 may in the form of component of the tracking device that is perceptible to the user and exists for another purpose, such as a camera lens of the device, a power light, or a corner or other aspect of the casing of the eye tracking device having a known geometric relationship to the sensor.

Figure 2D:
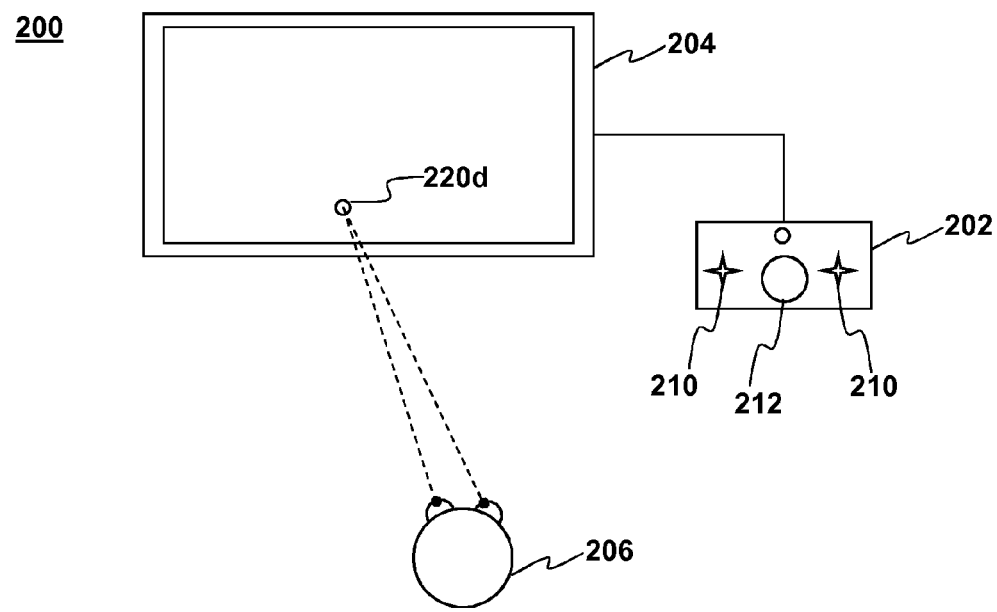

As depicted in FIG. 2D, calibration process may then involve another visual calibration target 220d that is output to the display device 204. This display target 220d may define another gaze point in an image at a different location from the display targets 220a and 220b, and eye tracking data may again be gathered with the eye tracking device 202 while the user 206 gazes at this target, and this additional eye tracking data may correlated with the additional calibration target 220d.

The data gathered during the calibration process depicted in FIGS. 2A-2D may be analyzed in order to determined one or more calibration parameters of the system setup. For example, a computing device that is coupled to the sensor 212 may receive the eye tracking data gathered during the calibration process and analyze the data to determine one or more geometric parameters of the system, such as display screen size of the display device 204 and/or relative location of the display device. By way of example, these parameters may be determined by estimating a parameter that best fits the eye tracking data gathered during the calibration process and the known relative locations of the calibration targets (i.e., the relative location in the image of the gaze point defined by each display target 220a,b,d, and the relative location to the sensor 212 of the gaze point defined by the sensor target 222). The fit may be determined, for example, using numerical optimization or statistical techniques such as curve fitting, regression analysis, and the like. The determined geometric parameters of the system setup may then be used to calibrate future eye tracking to improve the accuracy of eye tracking. For example, an eye tracking system calibrated in accordance with the calibration process described above may be used to better determine where on a displayed image a user's gaze point lies.

It is noted that the additional information obtained from the eye tracking data that is correlated with the sensor target 222 attached to the eye tracking device may provide additional information that improves the accuracy of the calibration process than would be otherwise achieved using only display targets 220a,b,d, i.e., better accuracy than would be achieved if all of the calibration targets defined gaze points in images output to the display device 204. For example, while a calibration process using only such as a calibration sequence involving a series of dots output to a display alone might achieve results that are internally consistent, but not necessarily correct, and they inaccurately reflect reality with respect to how the system is actually set up, producing less than optimal eye tracking performance during subsequent eye tracking applications.

It is noted that the accuracy of the calibration process described above may be generally dependent upon the user 206 actually looking at each of the gaze points defined by the calibration targets 220a,b,d and 222 so that the eye tracking data gathered during the calibration process and correlated to each calibration target actually contains data of the user's eye directed at each visual target. Accordingly, the user 206 should be directed to gaze at each of the calibration targets during the calibration process, which can be accomplished in any of a variety of ways. By way of example, the calibration process may involve instructing the user 206 before or during the calibration process to look at each of the calibration targets. Instructing the user may be accomplished, for example, through audible or visual instructions included in a calibration program that outputs the calibration process, or by a simple instruction manual separately provided to the user 206.

It is further noted that that the example calibration process described above with reference to FIGS. 2A-2D may encompass many variations without departing from the spirit and scope of the principles embodied therein.

By way of example, any arbitrary number of visual calibration targets may be used during the process, include one or more display targets similar to targets 220*a,b,d*, as well as one or more sensor targets similar to target 222. Each unique gaze point defined by the visual targets may provide additional useful information in calibrating the tracking system for subsequent gaze tracking applications.

By way of further example, the different steps of the calibration process involving the different gaze points may be performed in any arbitrary order. Furthermore, in one example, the different steps of the calibration process may be performed in direct succession as a single calibration sequence that cycles through each of the calibration targets. However, in another example, they do not have to be part of a single sequence, but rather may be performed at different discontinuous times, so long as the system can correlate gathered eye tracking data to the appropriate target. Likewise, it will be appreciated that any of the calibration steps and/or gaze points may be multiplied, duplicated, etc.

Figure 3:
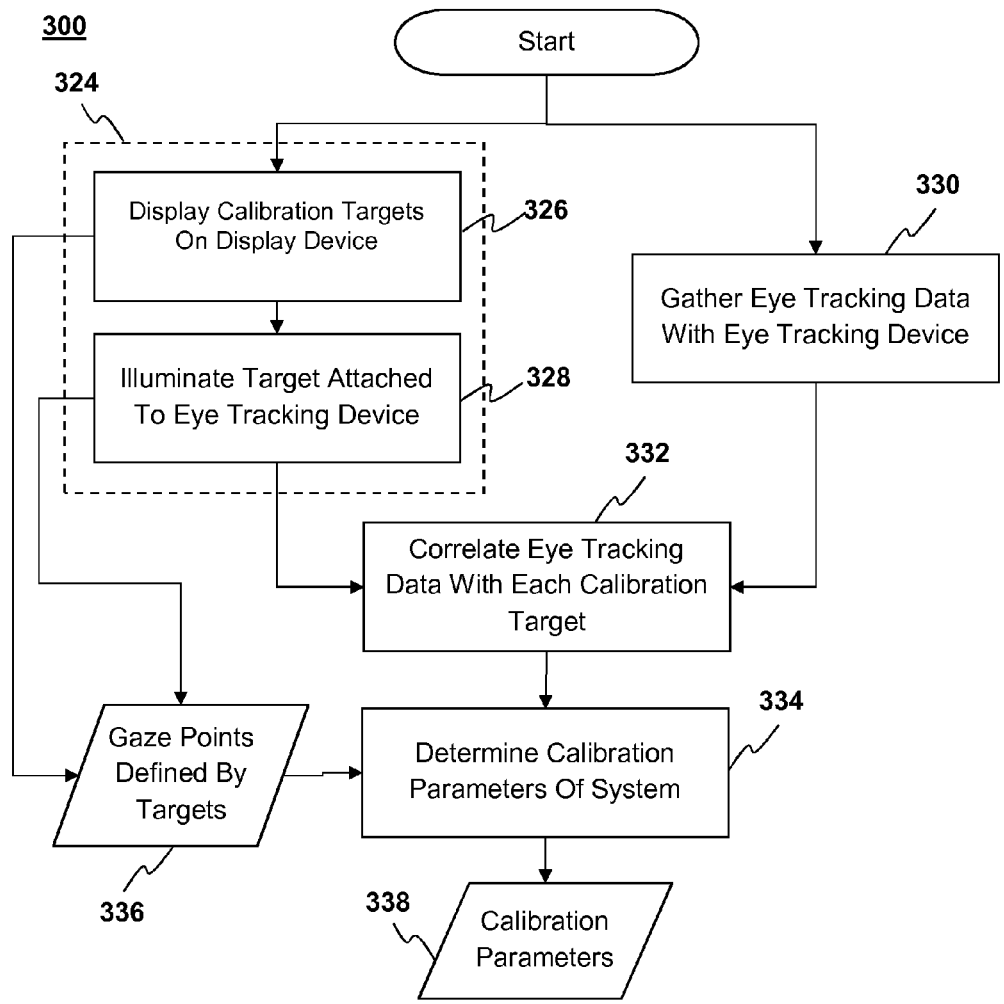
FIG. 3 is a flow diagram depicting an example method of determining calibration parameters using the calibration process depicted in FIGS. 2A-2D to illustrate various aspects of the present disclosure.

FIG. 3 depicts a flow diagram of a method 300 of calibrating a system for eye tracking in accordance with aspects of the present disclosure. The method 300 may involve a user looking at a plurality of visual calibration targets similar to the calibration process depicted in FIGS. 2A-2D. In one implementation, the example method 300 may be performed by a computing device that is coupled to an eye tracking device and a display device, such as the eye tracking device 202 and display device 204 depicted in FIGS. 2A-2D. The method 300 may involve a calibration process which uses one or more display targets which are output to a display device and one or more sensor targets which are attached to an eye tracking device. Each of these visible calibration targets may define a unique gaze point for a user to look at during the calibration process.

The example method 300 may include delivering various outputs 324 for the calibration process. The calibration process outputs 324 may include displaying each of the display targets 326 as images output to a display device. By way of example, and not by way of limitation, this may include outputting a plurality of differently located dots to the display device, whereby each of these dots defines a gaze point at a unique location on the display of the display device.

Delivering the calibration outputs 324 may also include illuminating one or more visible targets attached to the eye tracking device 328. By way of example, and not by way of limitation, this may involve sending a control signal to the eye tracking device that causes a visible light source of the eye tracking device, such as an LED, to be illuminated during a particular step of the calibration process. The illuminated sensor target may define a gaze point in the calibration process that has a known geometric relationship, i.e. distance and orientation, to the eye tracking device itself. For example, the sensor target may disposed at the location of the sensor itself, such, e.g., at the location of a lens of an infrared camera or at location proximate the lens.

Before and/or during the presentation of the calibration targets 326, 328, a user may be instructed to gaze at each of the targets for the calibration process. For example, the calibration process outputs 324 may also include one or more audible and/or visible cues which instruct the user to gaze at each of the targets or otherwise direct the user's gaze thereto. In one implementation, some or all of the calibration process may be provided as a game or otherwise integrated into another aspect of a computer application so that the process appears seamless to the user, thereby enhancing the user experience.

While each of the visible calibration targets are being displayed 326, 328, the example method 300 may also include gathering eye tracking data with the eye tracking device 330. Gathering the data with the eye tracking device 330 may include emitting light with a light source of the eye tracking device and detecting an area illuminated by light source with a sensor of the eye tracking device. The illuminated area may include a user gazing at each of the visual targets during the calibration process, and reflections of the emitted light off the user's eye(s) may be detected with the sensor. In one implementation, the emitted light is infrared light emitted from one or more infrared LEDS attached to the eye tracking device, and the area illuminated by the infrared light is detected with the sensor by capturing images of the area with an infrared camera. Accordingly, the eye tracking data may include images of a user's eyes gazing at the eye tracking device itself, or gazing at a gaze point having a known geometric relationship to the eye tracking device based on the sensor target output 328.

The method 300 may also include correlating the gathered eye tracking data with each of the calibration targets 332. For example, each portion of the data gathered with the eye tracking device during the calibration process may be correlated with a corresponding gaze point defined by a calibration target output while the data was gathered. The correlated eye tracking data may then be used to determine one or more calibration parameters 334 of the system for eye tracking. Determination of the calibration parameters 334 may be based upon relatively known locations of the gaze points 336 defined by each of the calibration targets (i.e., display targets' known relative locations within the output images 326 and the sensor target's known relative location with respect to the eye tracking device sensor). This determination 334 may include a determination one or more geometric parameters which best fit the gathered eye tracking data and correlated gaze point locations defined by the targets of the calibration process, e.g., using an algorithm which estimates parameters using numerical optimization or statistical techniques based on the data.

A wide variety of calibration parameters may be determined, including geometric parameters of the system setup and the user involve in the calibration process. For example, a relative location (i.e. distance and/or three-dimensional orientation) of the eye tracking device with respect to the display device may be determined, a screen size and/or aspect ratio of the display device may be determined, an iris size of a user, eye curvature, pupil depth relative to cornea, interpupillary distance (IPD), iris texture, or some combination thereof may be determined using the eye tracking data gathered during the calibration process. These calibration parameters 338 may then be used to calibrate an eye tracking application which uses the eye tracking device and/or display device. Moreover, because the eye tracking data may include not only data of eyes gazing a known points within a display image, but also gazing at a known point relative to the eye tracking device, the method 300 may better resolve ambiguities that might otherwise result from the large number of calibration parameters and setup parameters.

It is noted that many variations of the method 300 are possible. For example, rather than illuminating one or more visible lights attached to the eye tracking device 328, the calibration output 324 may simply involve instructing a user to look at a marking made on the tracking device or look at some other known point of the device, e.g., as described above with respect to FIG. 2C.

Figure 4:
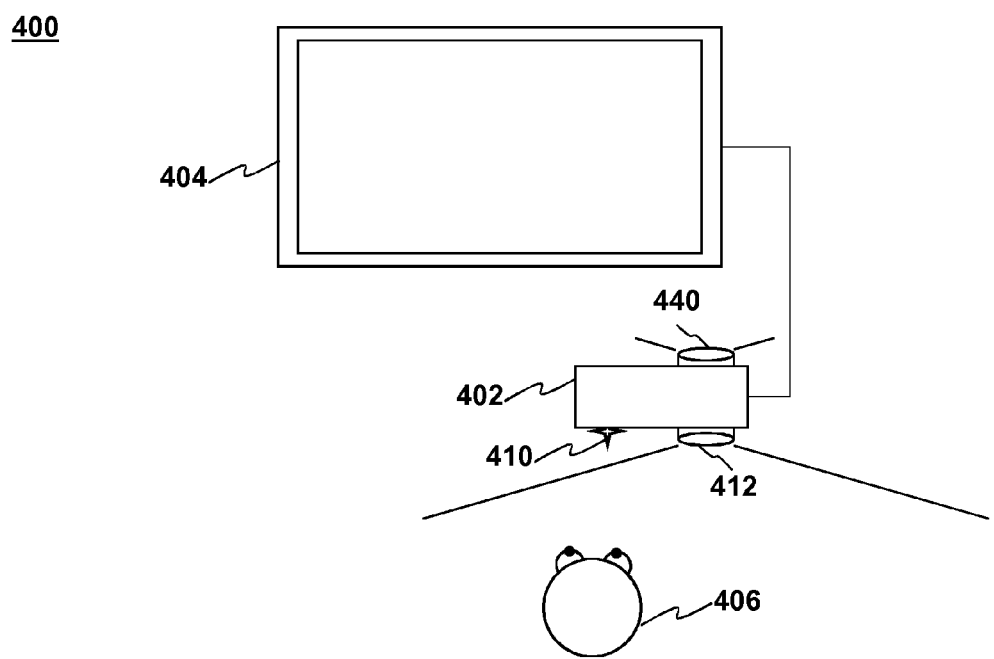
FIG. 4 is a schematic diagram depicting another example calibration process for a system that is similar to the systems depicted in FIGS. 1A-1C to illustrate various aspects of the present disclosure.

A schematic diagram of another example calibration process for a system for eye tracking 400 is depicted in FIG. 4 to illustrate various aspects of the present disclosure.

The example calibration process of FIG. 4 involves an additional sensor 440 on an eye tracking device 402, which gathers additional data relevant to the calibration of the system for eye tracking 400. Specifically, the example system 400 includes a display device 404 and an eye tracking device 402, wherein the eye tracking device 402 includes a light source 410, a first sensor 412 which is sensitive to light emitted from the light source 410, and a second sensor 440. The light source 410 and the sensor 412 of the eye tracking device 402 may be similar to those of the eye tracking devices 102 and 202 of FIGS. 1A-1C and 2A-2D. For example, the light source 410 may be an invisible light source such as one or more infrared LEDs, and the sensor 412 may be a sensor that detects infrared light, such as an infrared camera. The sensor 412 may operate in conjunction with the light source 402 to gather eye tracking data of a user 406, e.g., by illuminating the user's eyes with the light source 402 and capturing images of the user's illuminated eyes with the sensor 412.

The example tracking device 402 also includes an additional sensor 440, i.e. in addition to the sensor 412, which may capture additional calibration data calibrating the system, e.g., as set up with respect to the display device 404. For example, the second sensor 440 may be an additional camera that is oriented at a different angle from the infrared camera 412 and which is configured to capture images of the setup of the system 400. In one implementation, this camera is sensitive to the visible spectrum and is back-facing with respect to the eye tracking device 402, while the infrared camera 412 and the light source 410 are front-facing with respect to the eye tracking device 402. This allows the additional camera 440 to capture images of the display device 404 when the eye tracking device 402 is setup to gather eye tracking data and capture images of a user 406 watching the display device 404.

While the exact relative locations of the display device 404 and separate eye tracking device 402 may be setup dependent and may vary with different setups or system combinations, the back-facing camera 440 allows these two components to be set up in such a way that the tracking device can capture images of the display device with the back-facing camera 440, and capture images with the front-facing camera 412 of a user 406 who is looking the display device 404 and illuminated by the light source 410. For example, the tracking device 402 may be setup slightly in front of the display device 404 so that the back-facing camera 440 may capture images of the display device 404 in order to gather such additional calibration data.

It is noted that many variations of the example system 400 depicted in FIG. 4 are possible. For example, the back-facing camera 440 may be movably attached to the tracking device 402, such as with a pivotal or rotatable attachment to a casing which houses the tracking device components, so that the exact angle at which it captures images of the display device is adjustable to account for different setups. In another implementation, a different sensor may be used instead of or in addition to a back-facing camera. For example, a tilt sensor or other position sensor may be included in order to gather additional calibration information for the system 400.

Figure 5:
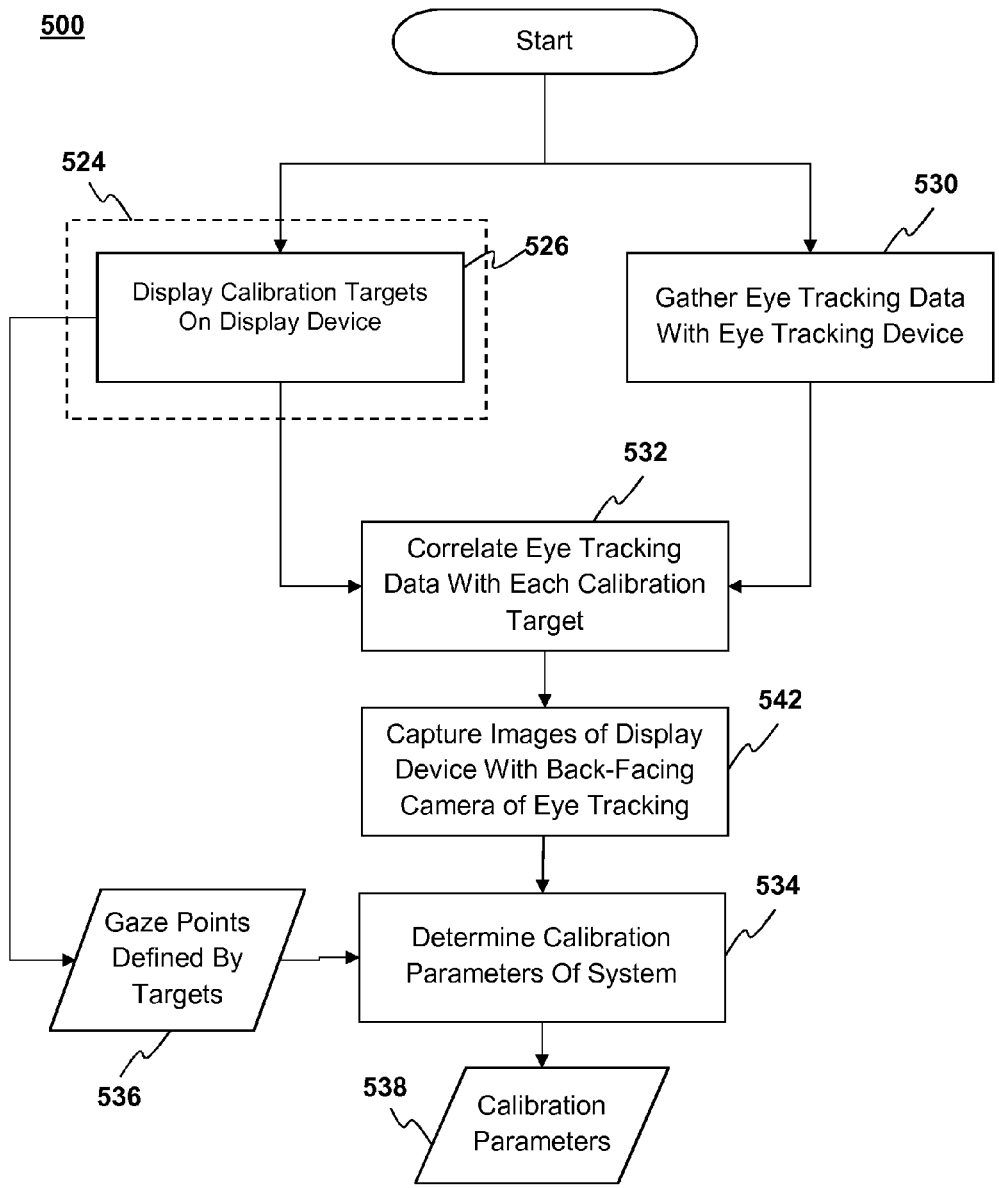
FIG. 5 is a flow diagram depicting another example method of determining calibration parameters using the calibration process depicted in FIG. 4 to illustrate various aspects of the present disclosure.

FIG. 5 depicts a flow diagram of a method 500 of calibrating a system for eye tracking in accordance with aspects of the present disclosure. The example method 500 may involve an eye tracking device having an additional sensor for gathering additional calibration data similar to the system 400 depicted in FIG. 4. The example method 500 may also share features in common with the method 300 depicted in FIG. 3. In particular, the illustrated method 500 is depicted as similar to method 300 except the sensor target output 328 of FIG. 3 is replaced with additional calibration data gathered with an additional sensor of an eye tracking device in the illustration of FIG. 5.

The example method 500 may include delivering various outputs 524 for the calibration process. The calibration process outputs 524 may include displaying each of the display targets 526 as images output to a display device, and each of these display targets may define a gaze point at a unique location on the display of the display device.

Delivering the calibration outputs 524 may also include illuminating one or more visible targets attached to the eye tracking device (not pictured), e.g., as described above with respect to FIG. 3. In alternative implementations, these sensor targets may be omitted because an additional sensor attached to the eye tracking device may gather sufficient calibration information to omit this step.

Before and/or during the presentation of the calibration targets 526, a user may be instructed to gaze at each of the targets for the calibration process, e.g. as described above, and while each of the visible calibration targets are being displayed 526, the example method 500 may also include gathering eye tracking data with the eye tracking device 530. Gathering the data with the eye tracking device 530 may include emitting light with a light source of the eye tracking device and detecting an area illuminated by light source with a first sensor of the eye tracking device. The illuminated area may include a user gazing at each of the visual targets during the calibration process, and reflections of the emitted light off the user's eye(s) may be detected with the first sensor. In one implementation, the emitted light is infrared light emitted from one or more infrared LEDS attached to the eye tracking device, and the area illuminated by the infrared light is detected with the first sensor by capturing images of the area with a front-facing infrared camera.

The method 500 may also include correlating the gathered eye tracking data with each of the calibration targets 532, e.g. as described above with respect to FIG. 3.

In addition to the eye tracking data gathered during the calibration process involving the visible calibration targets, the method 500 may also include gathering additional calibration data 542 with one or more additional sensors of the eye tracking device. This may include capturing an image of the display device with a back-facing camera of the eye tracking device. For example, this image may be captured while an image is being displayed on the display device, which may be the calibration images 526 or one or more other images. An example of capturing images of a display device using a camera for calibration of a system is described in U.S. Pat. No. 8,497,902 to Osman, the entire contents of which are herein incorporated by reference, and any of the techniques described in that document may be used in conjunction with a back-facing camera of the eye tracking device.

Specifically, a relative position of the display device 404 with respect to the eye tracking device 402 may, include displaying an image on the display device, estimating a first position and first orientation of the display device relative to the tracking device, once the tracking device has found the image on the display device with the additional sensor 440 (e.g., a rearward facing camera). The user may then be instructed to move the tracking device 402 to a new position and a second position and orientation of the display device 404 relative to the tracking device may be estimated, once the additional sensor 404 has found the image on the display device. The size of the display device 404 may then be determined using information gathered during the estimating of the first position and orientation and the estimating of the second position and orientation, and determining the orientation of the display device relative to tracking device 402.

In another implementation, this may involving capturing information from a tilt sensor of the eye tracking device. In yet another implementation, the eye tracking device may contain more than one additional sensor, and some combination of these may occur.

The correlated eye tracking data from 532 and the additional calibration data from 542 may then be used to determine one or more calibration parameters 534 of the system for eye tracking. Some or all of the determination of the calibration parameters 534 may be based upon relatively known locations of the gaze points 536 defined by each of the calibration targets, as described above with respect to FIG. 3. This determination may be alternatively or additionally be based at least in part on the additional calibration data obtained from the additional sensor of the eye tracking device. For example, images of the display device may be used at least in part to determine screen size and/or display device location relative to the eye tracking device. This determination 534 may include a determination one or more geometric parameters which best fit the gathered eye tracking data, additional calibration data, and/or correlated gaze point locations defined by the targets of the calibration process, e.g., using an algorithm which estimates parameters using numerical optimization or statistical techniques based on the data.

A wide variety of calibration parameters may be determined, and these calibration parameters 538 may then be used to calibrate an eye tracking application which uses the eye tracking device and/or display device. Moreover, because the eye tracking data may include not only data of eyes gazing a known points within a display image, but also additional calibration data obtained with the additional sensor of the eye tracking device, the method 500 may better resolve ambiguities that might otherwise result from the large number of calibration parameters and setup parameters.

Figure 6:
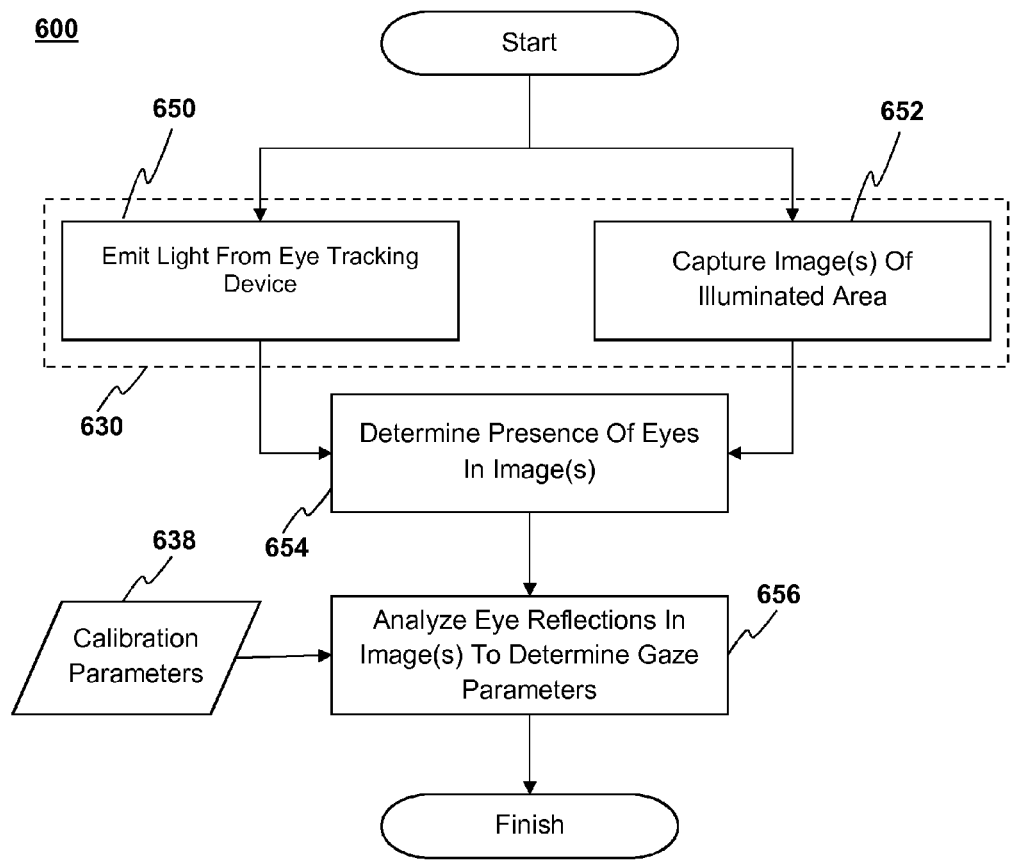
FIG. 6 is a flow diagram depicting an example of a method of eye tracking using previously determined eye tracking parameters to illustrate various aspects of the present disclosure.

An example of a calibrated eye tracking method 600 is depicted in FIG. 6 to illustrate various aspects of the present disclosure. The example method 600 may utilize determined calibration parameters, such as one or more calibration parameters determined by the methods depicted in FIG. 3 and/or FIG. 5 to track a user's eyes.

The example method 600 includes gathering eye tracking data with an eye tracking device 630, which may include emitting light from a light source 650 (e.g. infrared light) of the eye tracking device and detecting an area illuminated by the emitted light 652 (e.g. capturing one or more infrared images of the illuminated area). The images may be processed to determine a presence of eyes in the images 654, e.g., by identifying a face and/or by identifying corneal reflections of the emitted light in the images. Processing of the images may be performed, e.g., by a computing device coupled to the sensor of the eye tracking device which is configured to perform gaze tracking analysis of the gathered eye tracking data.

The images may be further processed to identify one or more gaze tracking parameters 656 using one or more previously determined calibration parameter 638. By way of example, this may involve identifying a dark spot in the images that is characteristic of a pupil and determining a gaze direction of the pupil relative to the eye location identified in the image. By way of further example, this may also involve determining a gaze point on a display device from the gaze direction, based on the calibration parameter 638.

Figure 7:
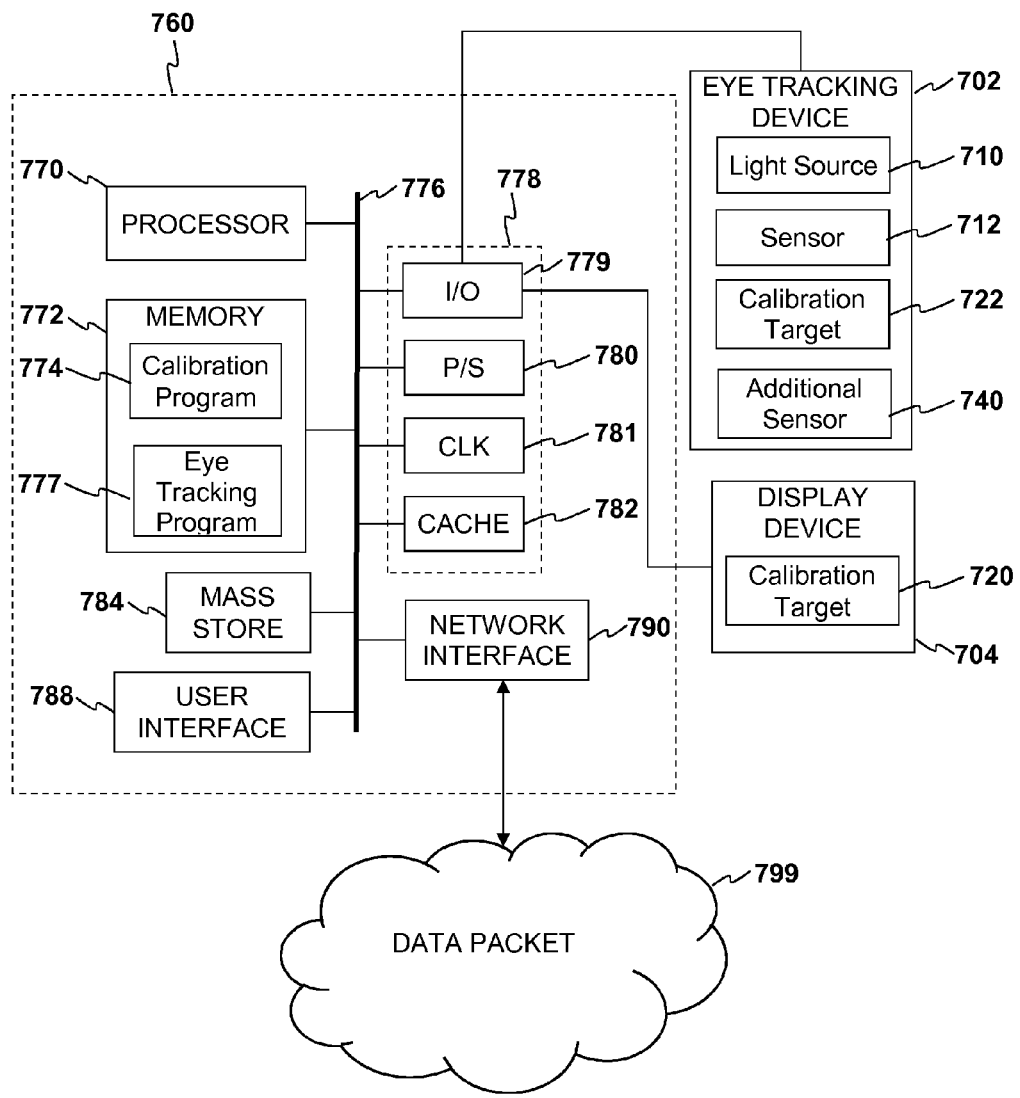
FIG. 7 is a block diagram depicting an example of a system for eye tracking to illustrate various aspects of the present disclosure.

FIG. 7 depicts an example system for eye tracking 700 to illustrate various aspects of the present disclosure. The example system 700 may include a computing device 760 which is coupled to an eye tracking device 702 and a display device 704 in order to perform eye gaze tracking and/or calibration for eye tracking in accordance with aspects of the present disclosure. The display device 786 may be in the form of a cathode ray tube (CRT), flat panel screen, touch screen, or other device that displays text, numerals, graphical symbols, or other visual objects. According to aspects of the present disclosure, the computing device 760 may be an embedded system, mobile phone, personal computer, tablet computer, portable game device, workstation, game console, and the like. Moreover, the computing device 760 may form an integral unit with the eye tracking device 702 or the display device 704, or it may be a separate unit in communication with the eye tracking device 702.

The eye tracking device 702 may be coupled to the computing device 760, and may include one or more light sources similar to light sources 210 of FIGS. 2A-2D. By way of example, and not by way of limitation, the light sources 710 may be invisible light sources in the form of one of more infrared LEDs, which may be configured to illuminate a user's eyes in order to gather eye tracking data with the sensor 712. The sensor 712 of the eye tracking device may be a detector which is sensitive to light emitted from the light source 710. By way of example, and not by way of limitation, the sensor 712 may be a camera sensitive to the light source such as an infrared camera, and the camera may be positioned relative to the eye tracking device and the light source so that it may capture images of an area illuminated by the light source 710.

In an implementation of aspect of the present disclosure, the eye tracking device 702 may also include one or more visible calibration targets 722 and/or one or more additional sensors 740 in addition to the sensor 712. For example, the calibration target 722 of the example eye tracking device 702 depicted in FIG. 7 may be a sensor target attached to the eye tracking device 702, and may defines a gaze point having a known location relative to the sensor 712, similar to the sensor target 222 of FIG. 2C. By way of example, the calibration target 722 may be a physical marking made on the device 702, or it may be a light source in the visible spectrum such as a visible LED, and may have a known relative location on the eye tracking device. The calibration target 722 of FIG. 7 may also be configured to receive control input from the computing device, such as an LED or small display which may be illuminated and turned off in accordance with a calibration process performed by the computing device 760.

In an implementation of an aspect of the present disclosure, the eye tracking device 702 may also include an additional sensor 740 instead of or in addition to the calibration target 722, and this additional sensor may have features in common with the additional sensor 440 of FIG. 4. By way of example, and not by way of limitation, the additional sensor 740 may be a camera angled in a different direction from the sensor 712, such as a back-facing camera sensitive to the visible spectrum, while the sensor 712 may be a front-facing camera sensitive to infrared light emitted from the light source 710.

The computing device 760 may be configured to operate in coordination with the eye tracking device 702 and the display device 704, in order to determine calibration parameters and perform eye gaze tracking in accordance with aspects of the present disclosure. The computing device 760 may include one or more processor units 770, which may be configured according to well-known architectures, such as, e.g., single-core, dual-core, quad-core, multi-core, processor-coprocessor, cell processor, and the like. The computing device 760 may also include one or more memory units 772 (e.g., RAM, DRAM, ROM, and the like).

The processor unit 770 may execute one or more programs, portions of which may be stored in the memory 772, and the processor 770 may be operatively coupled to the memory 772, e.g., by accessing the memory via a data bus 776. The program s may be configured to perform eye gaze tracking and determine one or more calibration parameters for the system 700. By way of example, and not by way of limitation, the programs may include calibration programs 774, execution of which may cause the system 700 to perform a method having one or more features in common with the method of FIG. 3 and/or the method of FIG. 5. By way of example, and not by way of limitation, the calibration program(s) 774 may include processor executable instructions which cause the system 700 to determine one or more calibration parameters of the system 700 from eye tracking data gathered with the sensor 712 during a calibration process. The calibration may involve a plurality if visible calibration targets which each define a unique gaze point having a known relative location, the calibration program 774 may further include instructions which cause outputs for the calibration process. By way of example, and not by way of limitation, the calibration program 774 may include instructions that, when executed, cause one or more calibration targets 720 to be output to the display device 704 as calibration images while the sensor 712 gathers eye tracking data. By way of further example, the calibration program 774 may include instructions that, when executed, cause the calibration target 722 to be illuminated while the sensor 712 gathers eye tracking data. The calibration program 774 may further include instructions that, when executed, cause the computing device 760 to analyze the eye tracking data gathered during this calibration process to determine one or more calibration parameters. This may include determining one or more geometric parameters of the system 700, such as, e.g., a size of the display device, a relative location of the display device 704 to the eye tracking device 702, or some combination thereof. The parameters may be determined by estimating one or more geometric parameters of the system which best fits both gathered eye tracking data (e.g., eye reflections and/or pupil locations contained in images captured with the sensor 712) the known relative locations of the gaze points defined by the calibration targets 720, 722.

The calibration programs 774 may also include instructions which cause the system to gather data from the additional sensor 740. By way of example, and not by way of limitation, this may involve capturing one or more images of the display device 704 with a back-facing camera of the eye tracking device 702, and analyzing this data to determine one or more calibration parameters of the system 700.

The programs may also include one or more eye tracking programs 777 containing processor executable instructions that, when executed, cause the system 700 to perform eye tracking with the eye tracking device 702. By way of example, and not by way of limitation, this may involve one or more features in common with the method depicted in FIG. 6. The eye tracking program 777 may perform calibrated eye tracking using one or more of the calibration parameters determined with the programs 774. The system 700 may also execute one or more general computer applications (not pictured), such as a video game, which may incorporate aspects of calibrated eye gaze tracking.

The computing device 760 may also include well-known support circuits 778, such as input/output (I/O) circuits 779, power supplies (P/S) 780, a clock (CLK) 781, and cache 782, which may communicate with other components of the system, e.g., via the bus 776. The computing device 760 may optionally include a mass storage device 784 such as a disk drive, CD-ROM drive, tape drive, flash memory, or the like, and the mass storage device 784 may store programs and/or data. The computing device 760 may also include a user interface 788 to facilitate interaction between the system 700 and a user. The user interface 788 may include a keyboard, mouse, light pen, game control pad, touch interface, or other device.

The computing device 760 may include a network interface 790, configured to enable the use of Wi-Fi, an Ethernet port, or other communication methods. The network interface 790 may incorporate suitable hardware, software, firmware or some combination thereof to facilitate communication via a telecommunications network. The network interface 790 may be configured to implement wired or wireless communication over local area networks and wide area networks such as the Internet. The computing device 760 may send and receive data and/or requests for files via one or more data packets 799 over a network.

It will readily be appreciated that variations on the components depicted in FIG. 7 are possible, and that various ones of these components may be implemented in hardware, software, firmware, or some combination thereof. For example, the some features or all features of the calibration programs contained in the memory 772 and executed by the processor 770 may instead be implemented via suitably configured hardware, such as one or more application specific integrated circuits (ASIC).

CONCLUSION

It is noted that aspects of the present disclosure have been described with reference to an eye tracking device that incledes a light source to illuminate eyes and tracked eyes based upon reflections. However, it is understood that other implementations are possible. For example, the eye tracking device may rely upon environmental lighting as opposed to an integrated light source to illuminate eyes. By way of further example, another sensor based eye tracking device, such as a contact lens based eye tracking system utilizing an IR camera may be used in implementations of the present disclosure.

It is further noted that aspects of the present disclosure have been described with reference to eye tracking devices that use infrared light sources, which has developed as a relatively standard light source for optical eye tracking techniques. However, it is understood that other implementations are possible. For example, in implementations of the present disclosure, other invisible light sources are possible, such as ultraviolet light. By way of further example, in implementations of the present disclosure, visible light sources are possible for eye illumination, although it may be desirable to use invisible light sources in order to avoid distracting a user.

Further aspects of the present disclosure have generally been described with reference to one display device; however, it is understood that other configurations are possible. For example, it is understood that the techniques described herein may be readily applied to configurations involving a plurality of display devices, such as dual-monitor computer setups, and calibration parameters involving the geometry of these multiple display devices may be determined.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "a", or "an" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method comprising:
   gathering eye tracking data during a calibration process with a sensor of an eye tracking device; and
   determining one or more calibration parameters from the eye tracking data,
   wherein the calibration process involves a plurality of visible calibration targets,
   wherein each said target defines a gaze point of the calibration process,
   wherein the plurality of targets includes one or more display targets and one or more sensor targets,
   wherein each of the one or more display targets defines a gaze point within an image output to a display device at a location known with respect to the image,
   wherein each of the one or more sensor targets defines a gaze point attached to the eye tracking device at a location known with respect to the eye tracking device, and
   wherein said determining the one or more calibration parameters includes determining one or more geometric parameters which fits the location of each of the gaze points defined by the one or more display targets, the location of each of the gaze points defined by the one or more sensor targets, and the eye tracking data gathered during the calibration process.

2. The method of claim 1, wherein the one or more sensor targets includes a visible light source attached to the eye tracking device.

3. The method of claim 2, further comprising illuminating the visible light source during the calibration process.

4. The method of claim 1, further comprising outputting each of the display targets to the display device.

5. The method of claim 1, further comprising instructing a user to gaze at each of the calibration targets.

6. The method of claim 1, further comprising, after said determining the one or more calibration parameters:
   gathering additional eye tracking data with the eye tracking device; and
   analyzing the additional eye tracking data to determine one or more eye gaze parameters of the user, wherein said analyzing the additional eye tracking data includes calibrating the additional eye tracking data with the one or more calibration parameters.

7. The method of claim 1, wherein the one or more calibration parameters determined from the eye tracking data includes a screen size of the display device.

8. The method of claim 1, wherein the one or more calibration parameters determined from the eye tracking data includes a location of the display device relative to the eye tracking device.

9. The method of claim 1, wherein the sensor is an infrared camera, and wherein said gathering the eye tracking data includes emitting infrared light from an infrared light source of the eye tracking device and capturing one or more images with the infrared camera of an area illuminated by said emitting the infrared light.

10. The method of claim 1, wherein the one or more display targets includes a plurality of display targets, each said display target defining a different gaze point within an image.

11. A system comprising:
    an eye tracking device having a sensor and one or more sensor targets; and
    a computing device coupled to the eye tracking device, wherein the system is configured to perform a method, the method comprising:
    gathering eye tracking data during a calibration process with the sensor of the eye tracking device; and
    determining, with the computing device, one or more calibration parameters from the eye tracking data,
    wherein the calibration process involves the one or more sensor targets and one or more display targets,
    wherein each said target defines a gaze point of the calibration process,
    wherein each of the one or more display targets defines a gaze point within an image output to a display device at a location known with respect to the image,
    wherein each of the one or more sensor targets defines a gaze point attached to the eye tracking device at a location known with respect to the eye tracking device, and
    wherein said determining the one or more calibration parameters includes determining one or more geometric parameters of the system which fits the location of each of the gaze points defined by the one or more display targets, the location of each of the gaze points defined by the one or more sensor targets, and the eye tracking data gathered during the calibration process.

12. The system of claim 11, wherein the eye tracking device further includes a visible light source, wherein the one or more sensor targets includes the visible light source.

13. The system of claim 12, wherein the method further comprises illuminating the visible light source during the calibration process.

14. The system of claim 11, wherein the method further comprises outputting each of the display targets to the display device.

15. The system of claim 11, wherein the method further comprises instructing a user to gaze at each of the calibration targets.

16. The system of claim 11, wherein the method further comprises, after said determining the one or more calibration parameters:
gathering additional eye tracking data with the eye tracking device; and
analyzing the additional eye tracking data with the computing device to determine one or more eye gaze parameters of the user, wherein said analyzing the additional eye tracking data includes calibrating the additional eye tracking data with the one or more calibration parameters.

17. The system of claim 11, wherein the one or more calibration parameters determined from the eye tracking data includes a screen size of the display device.

18. The system of claim 11, wherein the one or more calibration parameters determined from the eye tracking data includes a location of the display device relative to the eye tracking device.

19. The system of claim 11, wherein the eye tracking device further comprises one or more infrared light sources, wherein the sensor of the eye tracking device is an infrared camera, and wherein said gathering the eye tracking data includes emitting infrared light from the infrared light source and capturing one or more images with the infrared camera of an area illuminated by said emitting the infrared light.

20. The system of claim 11, wherein the one or more display targets includes a plurality of display targets, each said display target defining a different gaze point within an image.

21. The system of claim 11, wherein the one or more sensor targets includes a marking on the eye tracking device, wherein the method further comprises instructing a user to gaze at the marking during the calibration process.

22. A non-transitory computer readable medium having processor-executable instructions embodied therein, wherein execution of the instructions by a processor causes a processor to perform a method, the method comprising:
gathering eye tracking data during a calibration process with a sensor of an eye tracking device; and
determining one or more calibration parameters from the eye tracking data,
wherein the calibration process involves a plurality of visible calibration targets,
wherein each said target defines a gaze point of the calibration process,
wherein the plurality of targets includes one or more display targets and one or more sensor targets,
wherein each of the one or more display targets defines a gaze point within an image output to a display device at a location known with respect to the image,
wherein each of the one or more sensor targets defines a gaze point attached to the eye tracking device at a location known with respect to the eye tracking device, and
wherein said determining the one or more calibration parameters includes determining one or more geometric parameters which fits the location of each of the gaze points defined by the one or more display targets, the location of each of the gaze points defined by the one or more sensor targets, and the eye tracking data gathered during the calibration process.

23. A method comprising:
gathering eye tracking data during a calibration process with a first sensor of an eye tracking device;
gathering calibration data with a second sensor of an eye tracking device; and
determining one or more calibration parameters from the eye tracking data and the calibration data,
wherein the calibration process involves a plurality of visible calibration targets,
wherein each said target defines a gaze point of the calibration process,
wherein the plurality of targets includes one or more display targets,
wherein each of the one or more display targets defines a gaze point within an image output to a display device at a location known with respect to the image, and
wherein said determining the one or more calibration parameters includes determining one or more geometric parameters which fits the location of each of the gaze points defined by the one or more display targets, the calibration data gathered with the second sensor, and the eye tracking data gathered during the calibration process.

24. The method of claim 23, wherein the second sensor is a camera, wherein said gathering the calibration data includes capturing one or more images of the display device.

25. The method of claim 24, wherein said determining the one or more calibration parameters includes analyzing the one or more images of the display device to determine a screen size of the display device, a relative location of the display device, or a combination thereof.

26. The method of claim 24, wherein the first sensor is an infrared camera, and wherein said gathering the eye tracking data includes emitting infrared light from an infrared light source of the eye tracking device and capturing one or more images with the infrared camera of an area illuminated by said emitting the infrared light.

27. A system comprising:
an eye tracking device, the eye tracking device having one or more light sources, a front-facing camera that is sensitive to light emitted from the one or more light sources, and a back-facing camera, further comprising:
a computing device coupled to the eye tracking device, wherein the system is configured to perform a method, the method comprising:
gathering eye tracking data during a calibration process with the front-facing camera;
gathering calibration data with the back-facing camera; and
determining one or more calibration parameters from the eye tracking data and the calibration data,
wherein the calibration process involves a plurality of visible calibration targets,
wherein each said target defines a gaze point of the calibration process,
wherein the plurality of targets includes one or more display targets,
wherein each of the one or more display targets defines a gaze point within an image output to a display device at a location known with respect to the image, and
wherein said gathering the calibration data includes capturing one or more images of the display device wherein said determining the one or more calibration parameters includes determining one or more geometric parameters which fits the location of each of the gaze points defined by the one or more display targets, the calibration data gathered with the second sensor, and the eye tracking data gathered during the calibration process.

28. The system of claim 27, wherein the one or more light sources are infrared light sources, wherein the front-facing camera is an infrared camera, and wherein the back-facing camera is a visible light camera.

29. A non-transitory computer readable medium having processor-executable instructions embodied therein, wherein execution of the instructions by a processor causes a processor to perform a method, the method comprising:

gathering eye tracking data during a calibration process with a first sensor of an eye tracking device;

gathering calibration data with a second sensor of an eye tracking device; and determining one or more calibration parameters from the eye tracking data and the calibration data, wherein the calibration process involves a plurality of visible calibration targets, wherein each said target defines a gaze point of the calibration process, wherein the plurality of targets includes one or more display targets, wherein each of the one or more display targets defines a gaze point within an image output to a display device at a location known with respect to the image, and wherein said determining the one or more calibration parameters includes determining one or more geometric parameters which fits the location of each of the gaze points defined by the one or more display targets, the calibration data gathered with the second sensor, and the eye tracking data gathered during the calibration process.

* * * * *